(12) United States Patent
Cubb

(10) Patent No.: US 7,946,981 B1
(45) Date of Patent: May 24, 2011

(54) TWO-PIECE VIDEO LARYNGOSCOPE

(76) Inventor: Anthony Cubb, Kingwood, TX (US)

( * ) Notice: Subject to any disclaimer, the term of this patent is extended or adjusted under 35 U.S.C. 154(b) by 840 days.

(21) Appl. No.: 11/879,343

(22) Filed: Jul. 15, 2007

Related U.S. Application Data

(63) Continuation-in-part of application No. 10/693,206, filed on Oct. 23, 2003, now abandoned.

(51) Int. Cl.
*A61B 1/267* (2006.01)

(52) U.S. Cl. ........ 600/194; 600/120; 600/187; 600/188; 600/197; 600/199

(58) Field of Classification Search .................. 600/120, 600/162, 164–165, 185–199
See application file for complete search history.

(56) References Cited

U.S. PATENT DOCUMENTS

| | | | |
|---|---|---|---|
| 3,776,222 A | 12/1973 | Smiddy | |
| 3,913,568 A * | 10/1975 | Carpenter | 600/142 |
| 4,742,819 A * | 5/1988 | George | 600/109 |
| 5,203,320 A * | 4/1993 | Augustine | 600/187 |
| 5,287,848 A | 2/1994 | Cubb et al. | |
| 5,377,668 A | 1/1995 | Ehmsen et al. | |
| 5,665,052 A * | 9/1997 | Bullard | 600/194 |
| 5,800,344 A | 9/1998 | Wood, Sr. et al. | |
| 5,827,178 A * | 10/1998 | Berall | 600/185 |
| 5,840,013 A * | 11/1998 | Lee et al. | 600/114 |
| 5,879,289 A * | 3/1999 | Yarush et al. | 600/179 |
| 6,221,007 B1 * | 4/2001 | Green | 600/160 |
| 6,652,453 B2 | 11/2003 | Smith et al. | |
| 6,655,377 B2 * | 12/2003 | Pacey | 128/200.26 |
| 6,676,598 B2 | 1/2004 | Rudischhauser et al. | |
| 6,843,769 B1 * | 1/2005 | Gandarias | 600/189 |
| 6,890,298 B2 | 5/2005 | Berci et al. | |
| 6,929,600 B2 | 8/2005 | Hill | |
| 7,044,909 B2 | 5/2006 | Berci et al. | |
| 7,156,091 B2 | 1/2007 | Koyama et al. | |
| 7,182,728 B2 | 2/2007 | Cubb et al. | |
| 2002/0022769 A1 * | 2/2002 | Smith et al. | 600/188 |
| 2003/0195390 A1 | 10/2003 | Graumann | |
| 2004/0019256 A1 * | 1/2004 | Cubb et al. | 600/188 |
| 2006/0065268 A1 | 3/2006 | Koyama et al. | |
| 2007/0106121 A1 | 5/2007 | Yokota et al. | |
| 2007/0106122 A1 | 5/2007 | Yokota et al. | |

* cited by examiner

*Primary Examiner* — Matthew J Kasztejna
(74) *Attorney, Agent, or Firm* — Kenneth A. Roddy

(57) ABSTRACT

A two-piece video laryngoscope includes a disposable handle/blade unit having a handgrip portion with a cavity at the proximal end, a curved distal end portion extending from the handgrip portion terminating in a terminal face containing a LED and a lens and digital image sensor connected with a first connector in the cavity, and a tube receptacle channel extending distally along the dorsal surface of and a vacuum/oxygen passageway extending through the curved distal end portion; and a power/video module releasably engaged in the cavity having a flat panel display pivotally mounted at the proximal end thereof and containing a rechargeable battery and electrical and video circuitry connected with a second connector. An endotracheal tube is received and releasably retained in the tube receptacle channel in a preloaded condition. When assembled, the connectors are engaged to complete the electrical and video circuits and allow viewing of insertion and intubation.

10 Claims, 3 Drawing Sheets

TWO-PIECE VIDEO LARYNGOSCOPE

CROSS REFERENCE TO RELATED APPLICATION

This application is a Continuation-In-Part and claims the benefit of priority under 35 U.S.C. 120 of U.S. patent application Ser. No. 10/693,206 filed Oct. 23, 2003 now abandoned, and which is expressly incorporated herein by reference in its entirety.

BACKGROUND OF THE INVENTION

1. Field of the Invention

The present invention generally relates to intubation devices and instruments for accessing the laryngeal area of the human body and, more particularly, to a two-piece video laryngoscope having a power/video module with a small color flat panel display pivotally mounted at the proximal end thereof and a replaceable handle/blade unit connected thereto, that allows indirect external visualization of a patient's upper airway, during endotracheal intubation.

2. Background Art

Laryngoscopes are widely known and used in the medical field to facilitate endotracheal intubation of a patient during a respiratory emergency situation in order to provide airway patency and positive air pressure through the upper airway and the lungs, manually or through mechanical ventilation of the lungs to the injured person. Such laryngoscopes are also used during surgical procedures to maintain an open airway and provide ventilatory support during surgery under anesthesia. In the human anatomy, the epiglottis normally overlies the glottis opening into the larynx to prevent the passage of food into the trachea during eating. Thus, when undertaking an endotracheal intubation, it is necessary to displace the epiglottis from the glottal opening to permit the air tube to be inserted in between the vocal cords and subsequently into the trachea.

Various laryngoscope constructions are known. The more widely used laryngoscopes consist of an elongate rigid metal blade, which may be straight or curved, that is attached to and supported at the upper end of a handle. The blade is inserted through the mouth of the patient into the pharyngeal area to forcibly displace the tongue and epiglottis in the upward direction to permit direct visualization of the glottis through the mouth opening. Some traditional laryngoscopes commonly have a light source which is directed along the blade to illuminate the area beyond the end of the blade. Since the mouth and laryngeal area are at approximately 90° to each other, such laryngoscopes require that the patient's head be hyper extended in the backward direction to create a relatively straight path to permit direct visualization of the glottis by the operator of the laryngoscope. Substantial force by the operator is required to overcome the natural skeleto-musculature tendencies of the patient, and the operator is required to perform the procedure while located at the head of the patient. Additionally, if there is concern that the patient may have suffered spinal injuries, the technique for possible direct visualization of the glottis involves risk due to the potential for increased spinal injury from this procedure.

Typically, in a procedure using laryngoscopes having e a conventional straight or curved blade, the larynx may be viewed through the mouth opening from an observation point just above or behind the head of the patient by sighting generally along the axis of the blade. The endotracheal tube is inserted, either orally or trans-nasally, and passed alongside the blade, and finally through the glottis. This procedure is often made more difficult by the presence of bodily fluids on or in the larynx and trachea, which significantly reduces visibility.

This intubation procedure is also typically performed at the head of a bed in a medical care facility, necessitating removal of the headboard of the bed to create a space between the bed and the wall, and requiring the operator maneuvering him/herself through the numerous intravenous lines and monitor equipment to be able to stand between the wall and the head of the bed, in order to place the endotracheal tube within the patient's trachea.

Without visualization of anatomical structure, intubation of a patient during an emergency situation may require blind placement of an endotracheal tube based on freehand trial and error. Without proper positioning and guidance, the tubular members often cause trauma or injury to anatomical tissue, or missed intubation into the esophagus with potential fatal consequences.

Surgical instruments having means for indirect illumination and visualization of the pharyngeal areas of the body are known.

Smiddy, U.S. Pat. No. 3,776,222 and Carpenter, U.S. Pat. No. 3,913,568 disclose devices for endotracheal intubation which comprise flexible or articulatable tubular probes having internal fiber optics for lighting and viewing the internal areas of the body. The image-transmitting bundle passes through the handle to an eyepiece. As disclosed in those patents, the probes carry a slidably removable endotracheal tube surrounding their outer surfaces and the probe is directly inserted into the trachea to position the tube. Such devices obviously require the use of relatively large diameter endotracheal tubes in order to be carried on the tubular probe, and their use necessarily is limited to patients with sufficiently large airway passages to accommodate the combined size of the probe and endotracheal tube. Additionally, due to the flexible nature of the probes, it is difficult to manipulate the probe to displace the tongue and epiglottis to permit guidance during insertion of the tube into the trachea. These instruments require a high degree of skill and a concomitant degree of training to perform the procedure quickly, without injuring the patient. Additionally, because of expense, lack of portability, and sterilization requirements to prevent cross contamination among patients, these instruments are generally not available in a non-hospital setting.

Ehmsen et al, U.S. Pat. No. 5,377,668 discloses a fiberscope for endoscopic diagnostics and therapy constructed with one or more of a pivoted eyepiece, a cannula insertion assembly capable of housing a retractable fiber bundle and/or delivering distention fluid, a disposable sheath and seal assembly and an encasement for a fiber bundle. The distal end of the encased bundle can be advanced or withdrawn from its protective sheath. When advanced, it may be reoriented in direction by means of linkage to structure which can be manipulated from outside the instrument.

Lee et al, U.S. Pat. No. 5,840,013 discloses an endoscopic instrument for controlled introduction of tubular members in the body that includes a blade assembly having a blade for retracting or manipulating anatomical tissue, a tubular member in the nature of an endoscope including an elongate fiber optic probe, a control section mounting a proximal end of the probe, an eyepiece mounted to the control section and a handle.

My previous patent, Cubb et al, U.S. Pat. No. 5,287,848 is directed toward a one-piece instrument for endotracheal intubation including an upper handle portion and curved lower blade portion, which allows suction capabilities as well as direct visualization of the vocal cords and larynx. The endotracheal tube is preloaded into one of several bored chambers of the instrument, and a second port may be connected at the top of the device to equipment for suctioning. Direct visualization of the vocal cords, larynx, and upper airways is accomplished through fiberoptic bundles which bring the images to an eyepiece at the top handle portion of the device.

My previous patent, Cubb et al, U.S. Pat. No. 7,182,728, is directed toward an endotracheal intubation device that utilizes optical fibers and an eyepiece at the end of a gooseneck fiber conduit extending from the optical housing which can be bent into a plurality of angular orientations with respect to the housing, and has an open top channel on a scabbard attached to the housing that is partially obstructed by a plurality of spaced-apart, interdigitated fingers for receiving an endotracheal tube.

My previous Patent Application, Cubb, Ser. No. 10/693,206, filed Oct. 23, 2003 and published Apr. 28, 2005 as Published Application 2005/0090712, which the present application is a C-I-P of, and which is expressly incorporated herein by reference in its entirety, discloses a multiple function two-section laryngoscope for intubation of a patient's trachea. A reusable handle houses a rechargeable battery, electronic circuits that feed a distal digital image to a variable position LCD screen or viewing port, switches and low battery indicator light. Distally, the handle electrically couples with a disposable curved scabbard having a dorsal endotracheal tube channel with a wavy opening that allows preloading and gentle extraction of different size endotracheal tubes once the patient's trachea has been intubated. The scabbard's distal end has a distal sweeper that engages the epiglottis and exposes the glottis, an opening for the exit of a preloaded endotracheal tube, a LED light, a suction/oxygenation port, and a lens coupled with a CMOS digital imaging system. Safe LCD view of one or serial rapid intubations are possible by rapidly replacing for a clean disposable scabbard in case of multiple emergencies Koyama et al, U.S. Pat. No. 7,156,091, filed Nov. 12, 2004, discloses an oral airway configured to accommodate an intubation tube to be inserted into the trachea. The oral air way includes a generally rectangular main body portion with a tubular curved insertion portion having a circular hollow passage extending from the proximal end to the distal end thereof, a side of the distal end of which contacts the root of the tongue to secure the patients' airway. The distal end of the insertion portion has a LED powered by battery in the main body through electric wires. An image guide extends through the hollow passage for receiving and transmitting light reflected by the LED, and a CCD image-acquiring member connected with the image guide is disposed in the main body. An optical enlargement system provided between the proximal end of the image guide and the CCD form an enlarged image on the CCD. A controller in the main body displays the image on a LCD display that is disposed laterally of the main body. A substantially U-shaped tube guide groove extends along another side of the insertion portion for slidably receiving the tube after the curved insertion portion has been inserted into the patient's mouth and advancing the tube into the trachea and has a notch at the distal end thereof to change the advancing direction of the tube, and a slanting portion in the groove disposed opposite to the notch to direct the distal end of the tube toward the notch. The width of the groove opening is smaller than the diameter of the tube to form an elongate slit and is enlarged toward the inside of the groove such that the tube is removed from the oral airway by deforming the tube in the radial direction thereof.

Koyama et al, Published Application 2006/0065268, filed Sep. 25, 2005 and published Mar. 30, 2006, discloses an intubation assistance instrument with an imaging system similar to U.S. Pat. No. 7,156,091, wherein the insertion portion is detachably mounted or fixed to the generally rectangular main body with a plurality of screws which can be covered with elastic caps, and has an arcuate cross section and a longitudinal straight section with a curved section extending from the straight section to a tip portion at the distal end thereof, the curved section having laterally spaced inner and outer walls which define the intubation tube receiving groove, and the outer wall formed with a longitudinal arcuate cut out portion forming a rounded tip portion. Removal of the instrument from the main body requires loosening or removing the screws with a screwdriver or other tool.

Yokota et al, Published Application 2007/0106121, filed Oct. 24, 2006 and published May 10, 2007, discloses an intubation assistance apparatus including a main body and an intubation assistance instrument detachably mounted to the main body and an imaging system. The main body has a casing with an annular coupling portion fastened to the distal end by bolts or screws or integrally formed thereon having an internally threaded inner circumference. The intubation instrument is externally threaded at its proximal end and threadedly engaged at the distal end of the coupling and held thereon by an annular sleeve. Alternatively, the instrument may be attached by a ratchet mechanism, a bayonet mounting, a cam, locking claw or magnetically. The curved insertion section of the instrument has an internal scope guide bore extending longitudinally from the proximal end to the distal end located eccentrically to the left when viewed from the operator in which a laryngoscope is removably received, and an optically transparent plate-like tongue piece protruding from the distal end. A CCD image pickup device, one or more lenses arranged on the distal end of a fiber bundle, and a white LED are disposed within the distal end portion of the insertion section. The laryngoscope has an elongate body portion connected at its proximal end to the distal end of the main body by a connector that contains the control line for the LED and the signal line of the CCD. An image display is rotatably mounted on the proximal end portion of the main body to pivot about a horizontal axis. A C-shaped or U-shaped intubation tube receiving groove or guide is formed on the outer side surface of the insertion section to extend from the proximal end to the distal end for leading the intubation tube toward the trachea of the patient as it is inserted through the patient's mouth.

Yokota et al, Published Application 2007/0106122, filed Oct. 24, 2006 and published May 10, 2007 discloses an intubation assistance apparatus including a main body and an intubation assistance instrument substantially similar to the above described Published Application 007/0106122, and a second embodiment wherein the display is fixedly mounted on the proximal end portion of the main body.

Wood, Sr., et al, U.S. Pat. No. 5,800,344 discloses a video laryngoscope having an image sensor assembly mounted thereto for providing video imaging of a patient's airway passage. The laryngoscope includes an elongate body having a convex surface and distal end with a tip adapted for contact with tissue of an airway passage and an image sensor assembly mounted to the convex surface so that an image sensor of the assembly is angled away from a tissue contacted by the tip when the laryngoscope is in use. In one embodiment, the image sensor assembly is slidably mounted on a track formed on a curved section of the laryngoscope body so that sliding of the image sensor assembly along the track adjusts the distance of the assembly from a target, and further adjusting the orientation angle of the image sensor assembly.

Smith et al, U.S. Pat. No. 6,652,453 discloses a portable video laryngoscope for aiding in the examination of a patient by an observer relying entirely upon machine-generated data to derive medical conclusions. The device includes a probe and a handle, the probe having a proximal end connected to the handle and an articulating, adjustable distal end projecting therefrom, the handle includes a distal end connected to the proximal end of the probe. The distal end of the probe includes a generally ovoid, C-shaped gripping means having a pair of elongated grasping lips and an internal clamping assembly for controlling the gripping means. A digital camera is mounted to the distal end of the probe to generate digital machine data and a display is adjustably and releasably mounted on the proximal end of the handle whereby a 2-D visual display is provided to a human observer. The display has a first working position to permit line of sight insertion of the probe into the throat cavity, and a second working position in which the line of sight is blocked, so that the observer relies entirely upon machine generated data to derive medical conclusions.

Rudischhauser et al, U.S. Pat. No. 6,676,598 discloses a laryngoscope that includes a handle, a spatula arranged substantially transverse to the handle, and a coupling detachably fixing the spatula to the handle. An illumination light waveguide guides an illumination light signal and an image waveguide guides an image signal, both waveguides being attached to the spatula. The illumination light waveguide includes a proximal end having an illumination light entry opening, and the image waveguide includes a proximal end having an image exit opening, wherein the illumination light entry opening and the image exit opening are arranged in the area of the coupling. The handle includes, in the area of the coupling, an illumination light exit opening and an image entry opening which allow for the illumination light signal to couple into the illumination light waveguide from the handle, and for the image signal to couple out of the image waveguide. A centering element automatically aligns the image entry opening and the image exit opening precisely to each other.

Berci et al, U.S. Pat. Nos. 6,890,298 and 7,044,909 disclose a video laryngoscope with detachable light and image guides comprising; a blade detachably connected to a handle; a two-stem receptacle connector; a first light guide for transmitting illuminating light and terminated in the two-stem receptacle connector; a first image guide for transmitting reflected light and terminated in the two-stem receptacle connector; and a light and image guiding attachment detachably connectable to the handle. The light and image guiding attachment includes a two-stem plug connector that mates with the two-stem receptacle connector, a second light guide for transmitting light and terminated in the two-stem plug connector, a second image guide for transmitting reflected light and terminated in the two-stem plug connector, and a substantially rigid outer casing for encasing the second light guide and the second image guide. The first light guide and first image guide are in communication with the second light guide and second image guide respectively via the receptacle and plug connectors when in an engaged position.

Hill, U.S. Pat. No. 6,929,600 discloses a vision system for use with an endotracheal tube for obtaining an image of an inner cavity of a patient. The vision system comprises: (a) a stylet having a first end for placement within the cavity, a second end, and a flexible shaft disposed therebetween; (b) a module mounted adjacent to the second end of the stylet, the module having a monitor upon which the image is displayed; (c) an optical system disposed within the module and within the flexible shaft for providing light to illuminate a region proximal to the first end and for obtaining an image of the illuminated region for displaying on the monitor; and (d) an adjusting means for adjusting the vertical and horizontal position of the monitor.

Graumann, published application 20030195390, discloses a digital laryngoscope for visualization and exposure of anatomical structures required for endotracheal intubation. The device has a press formed blade unit with a reverse curvature/concave distal end fitted with an infrared LED mounted to the distal end and has a first member of a slide mount coupling mechanism at its proximal end for mounting it to a mating coupling mount on the proximal end of handle. The handle holds a metal tube contoured to fit the blade curvature behind the blade, which houses an optical image sensor unit, and contains a battery and digital color processor electronic circuits and has a mount at its distal end for receiving a RF Transmitter unit. The digital processor receives its input from the optical image sensor via wiring and sends it by wire to the RF transmitter unit, which transmits it to one or multiple remote wireless display color monitor screens fitted with a RF receiver unit. Alternatively, the RF transmitter may be replaced with a small LCD monitor that connects to the distal end of the handle.

SUMMARY OF THE INVENTION

The present invention overcomes the aforementioned difficulties, and is distinguished over the prior art in general, and these patents in particular, by a multifunction two-piece video laryngoscope that enables indirect external visualization of a patient's upper airway from various operator positions around the patient during endotracheal intubation of a patient's trachea during a respiratory emergency or as an elective procedure. The two-piece video laryngoscope includes a disposable handle/blade unit, and a power/video module releasably engaged in the proximal end of the handle/blade unit. The handle/blade unit is a unitary integrally formed member having a handgrip portion at the proximal end for accommodating a user's hand and a contiguous curved distal end portion extending distally from the handgrip portion sized and shaped to accommodate the anatomical contour of the tongue and throat structures of the patient and terminating in a terminal face, and an epiglottis sweeper and endotracheal guide at the terminal end. The handgrip portion has an inwardly extending cavity at the proximal end with a first connector in the cavity for receiving and operatively connecting the power/video module, a cool bright light emitting diode (LED) sealingly disposed in the terminal face connected in electrical communication with the first connector by a conduit, a lens and a digital image sensor sealingly disposed in the terminal face connected in image data transmitting communication with the first connector by a conduit, and an endotracheal tube receptacle channel extending distally along the dorsal surface of the curved distal end portion having an open entry end adjacent to said handgrip portion and an open exit end at the terminal face.

The endotracheal tube receptacle channel has a transversely generally arcuate or half-ovoid bottom segment that extends along the dorsal surface of the handle/blade unit starting a short distance from the handgrip portion and along the curved distal end portion to the terminal end, and at least one transversely curved generally arcuate top segment that extends partially over, and a distance along, the bottom segment of the channel. A plastic endotracheal tube is slidably received and releasably retained in the channel in a preloaded condition such that the exit direction of the tube is predictable during insertion of the handle/blade unit into the patient's mouth and throat. An air passageway in fluid communication with a vacuum/oxygen connector and control orifice beneath the cavity extends through the interior of the handle/blade unit to the terminal end for providing suction or oxygen.

The power/video module has a housing sized and shaped to be received in the proximal end of the handle/blade unit cavity and a second connector thereon for mating engagement with the first connector, a small color flat panel display including image decoding circuitry pivotally mounted at the proximal end thereof, a rechargeable battery power source and electrical and video circuitry contained in the housing connected with the second connector and with the viewing screen display circuitry, and indicator LEDs and control switches on the exterior of the housing connected with the electrical and video circuitry. The exterior of the power/video module also has control switches, condition indicator LEDs, a battery recharging jack and an auxiliary video output jack.

When the power/video module is pressed into the cavity of the handle/blade unit, the first and second connectors become engaged to connect the rechargeable battery power source and the electrical and video circuitry in communication with the flat panel viewing screen and the light emitting diode (LED) and digital image sensor in the terminal face to allow illumination of an area adjacent to the terminal face and transmission of digital images to the flat panel display viewing screen during insertion and intubation procedures.

The present video laryngoscope allows an operator to quickly and accurately accomplish indirect visual endotracheal intubation by manipulation of soft tissue in the mouth and does not require force by the operator to overcome the natural skeleto-musculature tendencies of the patient.

Another feature and advantage of the present video laryngoscope is that it provides clear indirect visualization of upper laryngeal structures via a color flat panel display viewing screen for ease of viewing by the practitioner from a diversity of position relative to the patient during the intubation process, and a safe distance away from possible hazardous materials in traumatized patients.

Another feature and advantage of the present video laryngoscope is that it does not require the operator to utilize an eyepiece or place their face close to the patients mouth for visualization of the upper laryngeal structures during the intubation process, thereby reducing the operator's exposure to infectious diseases, bodily secretions, and other bacterial matter which may be coughed up by the patient.

Another feature and advantage of the present video laryngoscope is that it allows the operator to be positioned not only at the patient's head while performing an intubation, but also permits endotracheal tube placement by the operator from different positions relative to the patient's location and orientation, such as the side of a bed in a medical care facility, and in tight or narrow spaces, such as intubating victims involved in vehicle accidents and mass casualties.

Another feature and advantage of the present video laryngoscope is that it allows for the simultaneous suctioning of bodily fluids from the throat area to eliminate obstructions from the field of view necessary for intubation or to provide oxygen to the patient while performing an intubation.

Another feature and advantage of the video laryngoscope is that it requires no hyperextension or only minimal hyperextension of the neck of the patient and facilitates intubation of difficult patients with possible cervical spine or neck injury with a protective neck collar in place, and thereby significantly reduces the potential of neck or cervical spine injuries, which can lead to further neck, spine, and spinal cord damage, and even paralysis by repositioning of the patient's neck.

Another feature and advantage of the video laryngoscope is that it requires no hyperextension or only minimal hyperextension of the neck of the patient and facilitates intubation of having a short, obese neck with an interiorly located upper airway.

Another feature an advantage of the video laryngoscope is that it can effectively accommodate different diameters of endotracheal tubes, according to the individual patient's needs.

Another feature an advantage of the video laryngoscope is that it can effectively accommodate preloading of an endotracheal tube to place it in a ready position for final insertion from a short distance from the target organs, the vocal cords.

Another feature an advantage of the video laryngoscope is that it has a detachable handle/blade unit, which is disposable to minimize the potential of cross contamination between patients and exposure of one patient by another patient infected by diseases such as HIV, hepatitis, or tuberculosis, among others.

Another feature and advantage is that the video laryngoscope is simple in construction, inexpensive to manufacture, rugged and reliable in operation, and suitable for use in an elective procedure in a hospital setting and during respiratory emergencies involving multiple victims with severe respiratory compromise necessitating multiple, simultaneous and/or rapidly sequential intubations.

Another feature and advantage is that the video laryngoscope is provided with an auxiliary video output port, which can be connected to auxiliary viewing or recording devices for auxiliary video capture and documentation of the intubation process.

A further feature and advantage is that the video laryngoscope is extremely lightweight, hand-held, self-powered with a long-lasting rechargeable power source, and allows long and continuous operation in case of catastrophe, rescue operations and mass casualties and military needs.

A still further feature and advantage is that the video laryngoscope is user friendly and can be easily and efficiently used by a practitioner with basic training.

Other features and advantages of the invention will become apparent from time to time throughout the specification and claims as hereinafter related.

DESCRIPTION OF THE PREFERRED EMBODIMENT

Figure 1:
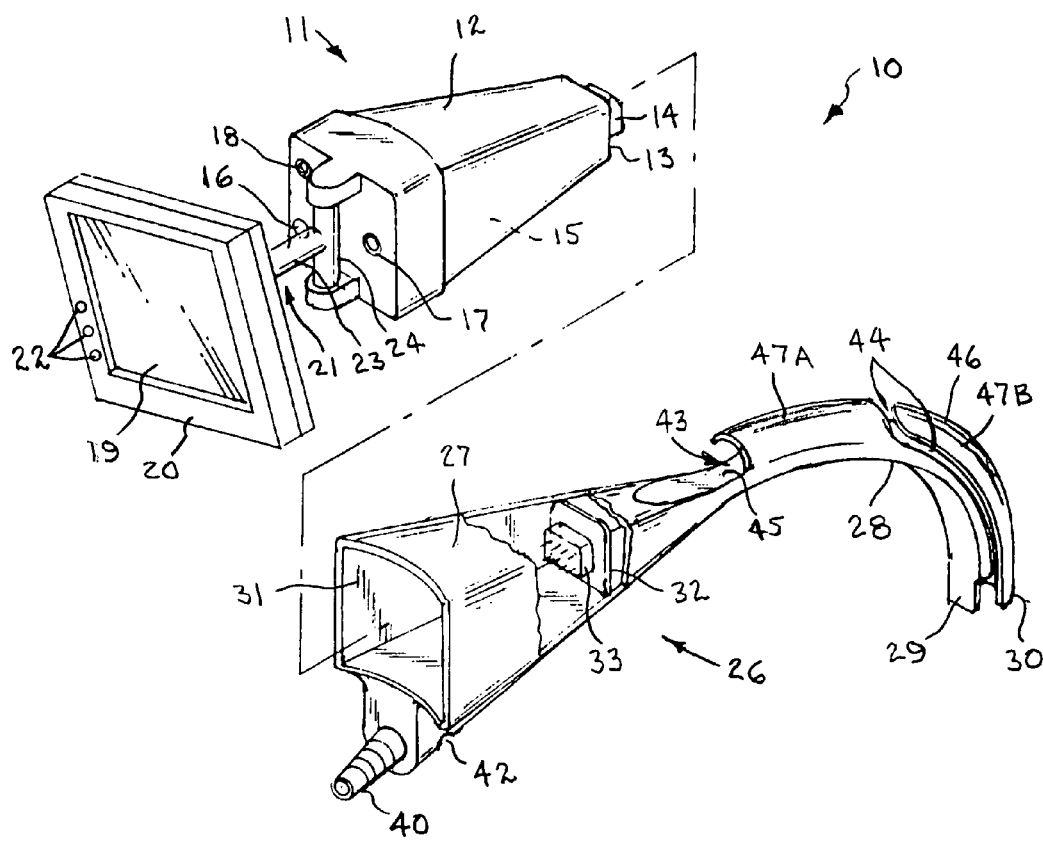
FIG. 1 is an exploded perspective view of the two-piece video laryngoscope in accordance with the present invention, shown with the power/video module and handle/blade unit in a disconnected condition, and with a portion of the handle/blade unit cut away to show the inner wall and connector at the end of the cavity.
Figure 2:
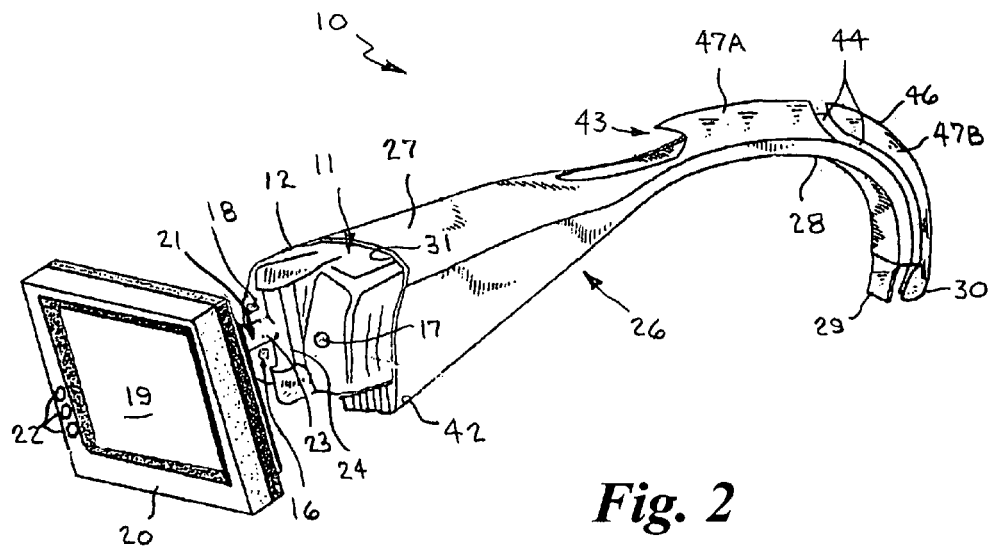
FIG. 2 is a perspective view of the two-piece video laryngoscope seen from the proximal end and right hand side, shown with the components in a connected condition.
Figure 3:
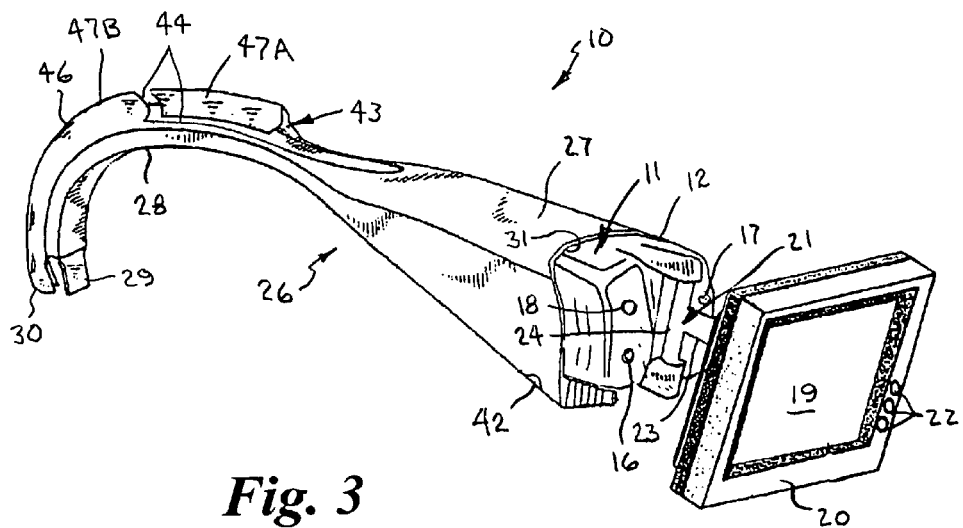
FIG. 3 is a perspective view of the two-piece video laryngoscope seen from the proximal end and left hand side, shown with the components in a connected condition.
Figure 5:
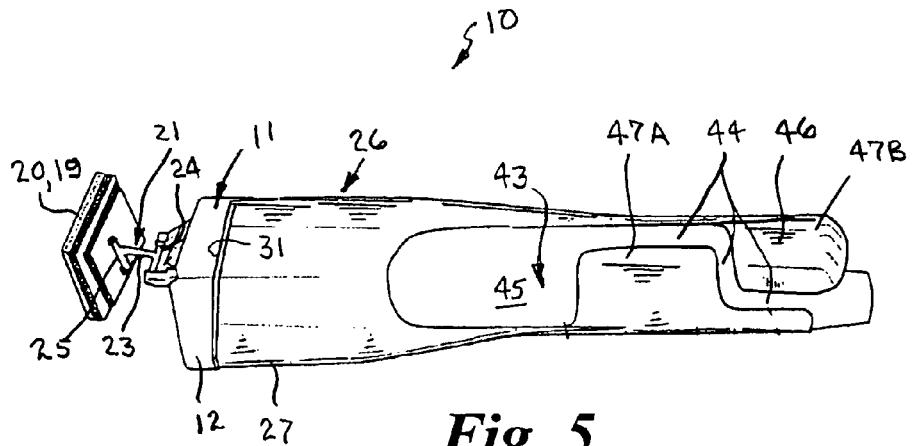
FIG. 5 is a top plan view of the two-piece video laryngoscope, more clearly showing the slot configuration that segments the top portion of the endotracheal tube channel.

Referring now to FIGS. 1-6, the present invention is a two-piece video laryngoscope 10 for use during endotracheal intubation that enables indirect external visualization of a patient's upper airway from various operator positions around the patient. The two-piece video laryngoscope 10 includes a lightweight disposable handle/blade unit 26 and a power/video module 11 with a pivotally mounted flat panel display viewing screen 19 at the proximal end thereof, which is releasably engaged in the proximal end of the handle/blade unit. FIG. 1 shows the components in a disconnected condition, and FIGS. 2-5 show the components in the connected condition.

The power/video module 11 has generally rectangular outer housing 12 that slightly tapers rearwardly and terminates in a rear wall 13 having a first female or male pin connector 14 mounted thereon. As represented by the reference numeral 15, the housing 12 of the power/video module 11 contains a rechargeable battery power supply and at least one circuit board or IC chip with electrical circuits and digital image I/O processing circuits for providing the digital image processing functions are connected with the connector 14 through and on-off button switch 16. The electrical circuitry and digital image processing circuitry are conventional and known to those skilled in the art of digital imaging, and therefore are not shown or described in detail. The on-off button switch 16 is shown somewhat schematically and is shown mounted on the front end of the housing 12 for purposes of example only, but may be mounted elsewhere. An AC/DC electrical jack or recharging connector 17 is disposed on the housing 12 in a position easily accessible to the operator and is connected in electrical communication with the battery 15 for connecting a source of power for recharging the battery using standard alternating current (AC) or direct current (DC). The recharging connector 17 is shown somewhat schematically, and shown mounted on the front end of the housing for purposes of example only, but may be mounted elsewhere. An RCA video output jack or connector 18 is disposed on the housing 12 in a position easily accessible to the operator and is operatively connected with the connector 14 to provide an auxiliary video output connection for connecting auxiliary viewing or recording devices.

The small color flat panel display screen 19 and associated digital image decoding circuitry are housed in a surrounding frame 20 that is pivotally mounted at the proximal end of the housing 12 by a hinge/swivel mounting mechanism 21 so as to be manually positioned in various angular positions. The small color flat panel display screen 19 may be a liquid crystal display (LCD or a plasma display panel (PDP). The video screen housing 20 may be provided with several low-intensity light-emitting diodes (LEDs) 22 connected with the battery circuit that indicate the condition or state of charge of the battery 15. The viewing screen image decoding circuitry and indicator LEDs 22 are connected with the electrical and video circuitry 15 contained in the housing 12 by one or more wires or conduits (not shown), as described below.

In the illustrated example, the hinge/swivel mounting mechanism 21 is a pivot arm having a central tubular member 23 with a first transverse pivot rod 24 at one end that is pivotally mounted at the front end of the housing 12 of the power/video module 11 to pivot left or right with respect to the housing, and a second transverse pivot rod 25 at the opposed end disposed in a plane normal to first pivot rod that is pivotally mounted on the back side of the frame 20 of the display screen 19 to allow the display screen to be pivotally adjusted at angular positions relative to a vertical plane for optimal viewing. One or more wires or conduits (not shown) extend through the tubular member 23 to connect the electrical and video circuitry 15 in the power/video module 11 with the electrical and display screen image decoding circuitry of the video display screen 19. It should be understood that the hinge/swivel mounting mechanism 21 shown and described is for purposes of example only, and not limited thereto, and that other hinge/swivel mechanisms may be used to allow the display screen to be manually positioned to achieve a desired viewing orientation. It should also be understood that the wires or conduits (not shown) connecting the electrical and video circuitry 15 in the power/video module 11 with the electrical and display screen image decoding circuitry of the display screen 19 may be disposed exterior of the hinge/swivel mounting mechanism 21, and that the image decoding circuitry may be disposed in the power/video module 11 rather than in the frame of the video display screen.

The handle/blade unit 26 is preferably integrally formed of a hard polymer material and has a handgrip portion 27 at the proximal end sized and shaped to accommodate an operator's hand, and an anatomically curved distal end portion 28 sized and shaped to accommodate the anatomical contour of the tongue and throat structures. The curvature configuration of the curved distal end portion 28 is conventional in the art, typically a smooth 90° curve, approximately. The underside of the curved distal end portion 28 has a short generally rectangular extension at its bottom end sized and shaped to serve as an epiglottis sweeper 29. The bottom end of the curved distal end portion 28 also has a short generally arcuate extension disposed opposite the epiglottis sweeper 29 that serves as an endotracheal tube guide 30.

As seen on FIG. 1, a cavity 31 extends inwardly from the proximal end of the handgrip portion 27 and terminates in an inner end wall 32. A second mating male or female pin connector 33 is mounted on the inner end wall 32 inside the cavity 17. The cavity 31 is sized and shaped to receive the outer housing 12 of the power/video module 11. It should be understood that the connectors 14 and 33 are mating connectors, one being a female connector and other being a male connector, i.e., the rear wall 13 of the power/video module 11 may be provided with a female connector and the inner wall 32 of the cavity 31 may be provided with a male connector.

Figure 4:
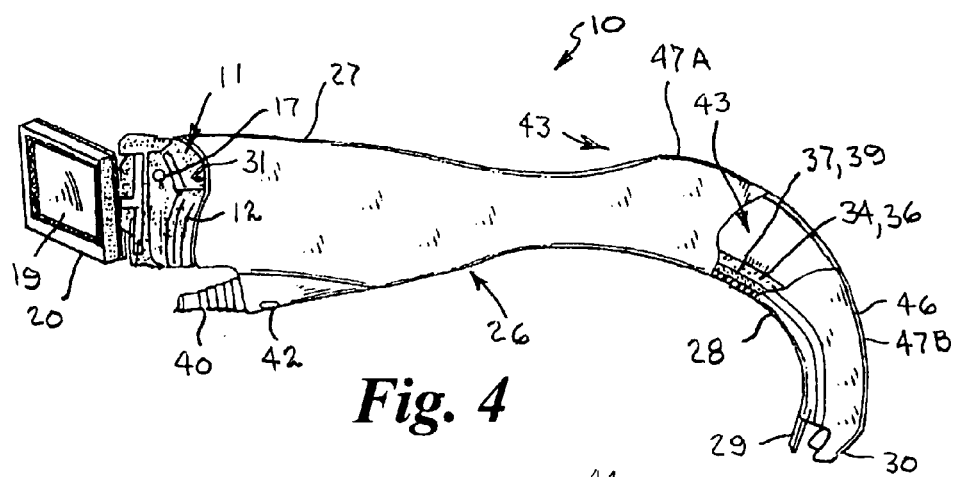
FIG. 4 is a side elevation view of the two-piece video laryngoscope, shown with a portion of the curved distal end portion cut away to show the endotracheal tube passageway and image conducting passageway and conduit.
Figure 6:
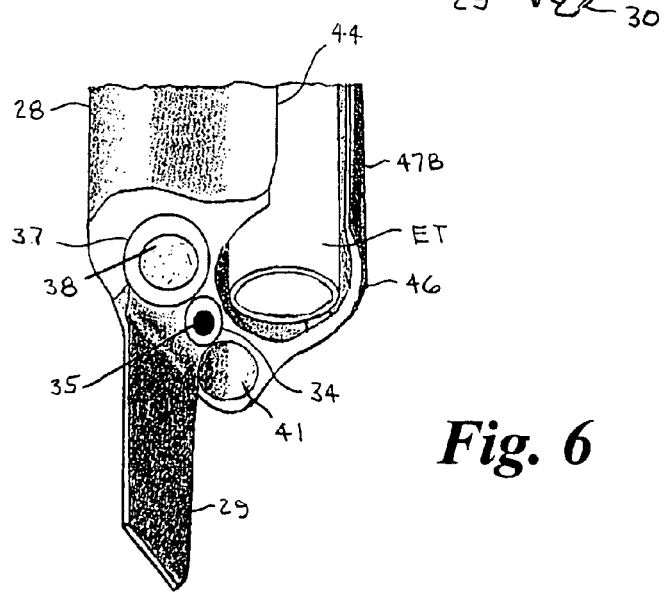
FIG. 6 is an enlarged partial perspective view of the bottom end of the curved distal end portion of the handle/blade unit, showing the epiglottis sweeper extension, and with the endotracheal tube guide extension removed to show the air passageway, the light emitting diode, and the lens and digital image sensor, represented somewhat schematically.

As best seen in FIGS. 4 and 6, the lower portion of the handle/blade unit 26 has a central image conduction passageway 34 that extends rearward through the interior of the curved distal end portion 28 from a point adjacent to the inner wall 32 and terminates in an open end. As represented somewhat schematically, a lens and CMOS digital image sensor 35 are sealingly engaged in the open end at the terminal face of the curved distal end portion. The lens is a wide-angle lens with a short focal point to bring a clear image at a short distance from the target area, the glottis/vocal cords, to the CMOS image sensor chip. An analog or digital image data conducting conduit 36 is disposed in the passageway 34 and has a proximal end connected with the connector 33 on the inner end wall 32 and a distal end connected with the CMOS digital image sensor 35. Although a CMOS digital image sensor (complementary metal oxide semiconductor) is preferred, it should be understood that other types of digital imaging sensors may be employed, such as a charge-coupled device (CCD).

The lower portion of the handle/blade unit 26 has an electrical conduction passageway 37 disposed in generally parallel laterally spaced relation to the passageway 34, that extends rearward through the interior of the curved distal end portion 28 from a point adjacent to the inner wall 32 and terminates in an open end, and a cool bright light emitting diode (LED) 38 is sealingly engaged in the open end at the terminal face of the curved distal end portion. An electrical conduit 39 is disposed in the passageway 37 and has a proximal end connected with the connector 33 on the inner end wall 32 and a distal end connected with the LED 38 to supply current to the LED.

When the power/video module 11 is pressed into the cavity 31 of the handle/blade unit 26, the connector 14 at its back end becomes engaged and electrically and operatively connected with the connector 33 in the cavity to complete the electrical and digital imaging circuits and connect the rechargeable battery power source and the electrical and video circuitry 15 in communication with the display screen circuitry and the light emitting diode (LED) 38 and digital image sensor 35.

A vacuum/oxygen port connector 40 is disposed beneath the cavity 31 and is in fluid flow communication with an air passageway 41 that extends through interior of the handle/blade unit 26 beneath the inner wall 32 and the entire length of the curved distal end portion 28 and terminates at the terminal face in an open end disposed in generally laterally spaced relation to the image conduction passageway 34. A vacuum/oxygen control orifice 42 in fluid communication with the air passageway 41 is disposed on the underside of the handle/blade unit 26. To apply suction, the vacuum/oxygen port connector 40 is connected to an external vacuum source and finger occlusive pressure is applied to the control orifice 42 to close the orifice so that secretions and possibly foreign material in the throat may be drawn to the end of the curved distal end portion 28 and through the passageway 41, thereby eliminating the need for a suction catheter. Alternatively, the vacuum/oxygen port connector 40 may be connected to an external oxygen supply source and finger occlusive pressure applied to the control orifice 42 to close the orifice to supply oxygen.

A segmented endotracheal tube receptacle channel 43 for preloading a plastic endotracheal tube ET is formed on the top or dorsal surface of the curved distal portion 28 of the handle/blade unit 26 and extends rearwardly from the handgrip portion 27 along the entire length of the curved portion to the terminal end of the curved portion.

The segmented tube receptacle channel 43 is a generally semi-cylindrical configuration, segmented by a longitudinal slot 44 that defines a transversely generally arcuate or half-ovoid bottom segment 45, and a transversely generally arcuate segmented top segment 46 that extend longitudinally rearward from the handgrip portion 27 along the curved distal portion 28 of the handle/blade unit 26. The arcuate or half-ovoid bottom segment of the channel is continuous and extends along the top of the handle/blade unit 26 starting a short distance from the handgrip portion 27 and along the curved distal portion 28 to the terminal end. As best seen from the top in FIG. 5, the longitudinal slot 44 extends along the top of the handle/blade unit 26 from the front of the channel a distance along one side, a distance transversely across the top segment 46 to the opposite side, and then continues on the opposite side along the remainder of the curved distal portion 28 of the handle/blade unit 26 to the terminal end. The configuration of the slot 44 segments the top segment 46 of the channel into a first transversely curved tab portion 47A at the proximal end of the top segment that extends from one lateral side partially over, and a distance along, the curved bottom segment 45 of the channel, and a second transversely curved tab portion 47B separated therefrom that extends from the opposed lateral side partially over, and along the remainder of the curved bottom segment 45 of the channel. Thus, the first and second transversely curved tab portions 47A and 47B form an incomplete "ceiling" over the continuous curved bottom segment 45 of the channel 43. The second transversely curved tab portion 47B may extend a short distance beyond the terminal end of the bottom segment 45 of the channel to form the endotracheal tube guide 30.

The tube receptacle channel 43 and curved tab portions 47A and 47B of the segmented top segment 46 are sized so as to snugly, but releasably accommodate a range of different sizes or diameters of conventional endotracheal tubes ET of the type well known in the art. Such a tube may be pre-positioned within the segmented tube receptacle channel 43 by pushing it into the proximal open end of the segmented tube channel under the curved tab portions 47A and 47B of the top segment 46 of the channel and along the interior of the curved distal portion 28 of the handle/blade unit 26. As the distal end of the endotracheal tube engages the curved tab portions 47A and 47B of the top segment 46 of the channel and follows the curved profile of the curved distal portion 28, the endotracheal tube resiliently bends or flexes under tension and becomes resiliently biased within in the channel 43 so as to become snugly but releasably retained within the tube receptacle channel by the resilient biasing force. Pre-positioning the endotracheal tube in this manner is desirable so that the distal end of the tube is placed a short distance from the target area and the exit direction of the tube is predictable during insertion of the handle/blade unit 26 into a patient's mouth and throat.

Operation

The two-piece video laryngoscope 10 is assembled by pressing the power/video module 11 into the cavity 31 of the handle/blade unit 26 such that the female pin connector 14 becomes engaged and electrically and operatively connected with the male pin connector 33 to complete the electrical and digital imaging circuits and connect them with the battery 15 inside the power/video module 11 to supply power to the light emitting diode (LED) 38 and circuitry of the display screen 19, and the display screen is turned on.

A standard plastic endotracheal tube is pre-positioned within the segmented tube receptacle channel 43 by pushing it into the proximal open end of the segmented tube channel under the curved tab portions 47A and 47B of the top segment 46 of the channel and along the interior of the curved distal portion 28 of the handle/blade unit 26, as described above, so as to become snugly but releasably retained within the tube receptacle channel by the resilient biasing pressure. Once the endotracheal tube has been pre-loaded, the intubation procedure may be started.

The flat panel display screen 19 is positioned to visualize the intubation process, and the curved distal end portion 28 of the handle/blade unit 26 is then inserted through the mouth into the throat's passageway, so as to gently slide into a desired position by displacing the softer tissue of the tongue and reach the target area, the glottis. Unlike most conventional intubation devices, in most situations utilizing the present device, the patient's head and neck need not be forcefully tilted backwards at all for intubation, and only minimal force or no force is needed to slide the curved distal end portion 28 of the handle/blade unit 26 through a small opening of the mouth and gently follow the local anatomy to quickly find the target openings. The epiglottis sweeper 29 at the terminal end of the curved distal end portion 28 of the handle/blade unit 26 positions itself in front of the epiglottis and allows for a gentle anterior sweep, towards the mouth and teeth line. This maneuver allows the sweeper 29 to hold the epiglottis back and away from the exposed glottis opening.

Once in this position, suction may be applied by placing a finger over the vacuum/oxygen control orifice 42, and applying finger pressure to close the orifice so as to draw bodily fluid and possibly foreign material away from the glottis and larynx and through the air passageway 41. Alternatively, the vacuum/oxygen port connector 40 may be connected to an external oxygen supply source and finger occlusive pressure applied to the control orifice 22 to close the orifice to supply oxygen.

Advantageously, this entire procedure can be visualized via the display screen 19 by positioning the hinge/swivel mounting mechanism 21 and display screen to achieve the optimal viewing position and, if desired, an auxiliary viewing or recording device may be connected to the video output jack or connector 18 on the housing 12 of the power/video module 11 for auxiliary video capture and documentation of the procedure.

With the patient's larynx in view through the display screen assembly, the pre-loaded endotracheal tube is maneuvered by gently pushing it through the segmented channel 43 and out the bottom end such that the tube finds its short way through the glottic opening into the tracheal cavity of the patient, all the while being observed by the person performing the intubation.

Once the endotracheal tube has been properly positioned and secured within the tracheal cavity, the handle/blade unit 26 is retrieved by gently sliding it back along the endotracheal tube to reach the teeth line and holding it firmly in place. The handle/blade unit 10 can then be separated and removed from the endotracheal tube by applying gentle finger pressure between the endotracheal tube and the segmented channel 43 so as to gently pry or extract the endotracheal tube out of the channel 43 through the slot 44 that forms the segmented channel. After the handle/blade unit 26 has been separated from the endotracheal tube it can be removed and the endotracheal tube further secured so that ventilation of the patient may be begun.

The power/video module 11 may be removed from the handle/blade unit 26 by simply pulling it out from within the cavity 31. The process of intubation can be repeated as needed by simply connecting a new handle/blade unit 26 loaded with a fresh endotracheal tube onto the power/video module 11.

While this invention has been described fully and completely with special emphasis upon a preferred embodiment, it should be understood that within the scope of the appended claims the invention may be practiced otherwise than as specifically described herein.

The invention claimed is:

1. A two-piece digital video laryngoscope for use in endotracheal intubation of a patient's trachea, comprising:

a unitary integrally formed disposable handle/blade unit having a handgrip portion at a proximal end for accommodating a user's hand, a contiguous downwardly curved distal end portion extending distally from said handgrip portion in a smooth curvature of approximately 90° sized and shaped to accommodate the anatomical contour of the tongue and throat structures of the patient and terminating in a terminal face, a flat generally rectangular epiglottis sweeper extending a short distance beyond said terminal face of said curved distal end portion configured to be positioned in front of the epiglottis and gently swept toward the mouth and teeth line of the patient to hold the epiglottis back and away from the exposed glottis opening, an inwardly extending cavity at the proximal end of said handgrip portion, a first electrical/digital image data connector in said cavity, a light emitting diode sealingly disposed in said terminal face connected in electrical communication with said first electrical/digital image data connector by an electrical conduit extending through said curved distal end portion, a lens sealingly disposed in said terminal face, and a digital image sensor sealingly disposed in said terminal face connected in image data transmitting communication with said first electrical/digital image data connector by an image data conduit extending through said curved distal end portion;

an endotracheal tube receptacle channel extending distally along a dorsal surface of said curved distal end portion having an open entry end adjacent to said handgrip portion and an open exit end at said terminal face, said channel having a transversely generally arcuate or half-ovoid bottom segment that extends along the dorsal surface of the handle/blade unit starting a short distance from said handgrip portion and along said curved distal end portion to said terminal face and a segmented transversely curved generally arcuate top segment that extends partially over, and a distance along, said bottom segment of said channel;

said segmented transversely curved generally arcuate top segment having a first transversely curved generally arcuate tab segment that extends from one lateral side partially over and a distance along a proximal end portion of said bottom segment, and a second transversely curved generally arcuate tab segment longitudinally spaced from said first tab segment that extends from the opposite lateral side partially over and a distance along a distal end portion of said bottom segment, said second arcuate tab segment terminating in opposed spaced relation to said epiglottis sweeper to serve as an endotracheal tube guide, said first and said second transversely curved generally arcuate top segments defining a slot that extends distance along said one lateral side, transversely across said channel to said opposite lateral side, and along said opposite lateral side of said curved distal end portion to said terminal face;

a power/video module having a housing sized and shaped to be removably received in said cavity at the proximal end of said handgrip portion and a second electrical/digital image data connector thereon for mating engagement with said first electrical/digital image data connector, a color flat panel display including image decoding circuitry pivotally mounted at the proximal end thereof, a rechargeable battery power source and electrical and video circuitry contained in said housing connected with said second electrical/digital image data connector and with said display circuitry, and indicator LEDs and control switches on the exterior of said housing connected with said electrical and video circuitry;

said first and said second electrical/digital image data connectors being engaged when said power/video module is received in said cavity at the proximal end of said handgrip portion to connect said rechargeable battery power source and said electrical and video circuitry in communication with said display and said light emitting diode and said digital image sensor in said terminal face to illuminate an area adjacent to said terminal face and transmit digital images to said display during insertion and intubation procedures;

said endotracheal tube receptacle channel and said slot sized and shaped to slidably receive and releasably retain an endotracheal tube therein in a preloaded curved condition such that the tube is inserted with said handle/ blade unit into the patient's mouth and throat during insertion of the handle/blade unit into the patient's mouth and throat and thereafter advanced relative thereto in a predictable exit direction with said second arcuate tab segment serving as a guide; and said slot of sufficient size to facilitate separation and removal of said handle/blade unit from the endotracheal tube after intubation by manually applying finger pressure between the endotracheal tube and said endotracheal tube receptacle channel so as to gently pry or extract the endotracheal tube out of said channel through said slot.

2. The two-piece digital video laryngoscope according to claim 1, further comprising:

an air passageway extending through the interior of said handle/blade unit from the proximal end and terminating in an open end at said terminal face, and a vacuum/oxygen port connector disposed on the exterior of said handle/blade unit in fluid flow communication with said air passageway for selective connection to either of an external vacuum source or an external oxygen supply source; and vacuum/oxygen control means in fluid communication with said air passageway for controlling passage of air therethrough to either apply suction at said terminal face to draw secretions and foreign material in the throat area through said air passageway, or to supply oxygen to the throat area.

3. The two-piece digital video laryngoscope according to claim 2, wherein said vacuum/oxygen control means comprises a control orifice in fluid communication with said air passageway positioned on the exterior said handle/blade unit to receive a finger of the operator for manually controlling passage of air therethrough whereby finger occlusive pressure is applied to the control orifice to close the orifice to either apply suction or to supply oxygen to the throat area.

4. The two-piece digital video laryngoscope according to claim 1, further comprising:

a recharging jack on the exterior of said power/video module housing connected with said rechargeable battery for connecting an external electrical source to recharge said battery.

5. The two-piece digital video laryngoscope according to claim 1, further comprising:

an auxiliary video output jack on the exterior of said power/video module housing connected with said electrical and video circuitry for connecting auxiliary external viewing or recording devices.

6. The two-piece digital video laryngoscope according to claim 1, wherein said flat panel display is pivotally mounted at the proximal end of said power/video module housing by a tubular pivot arm mechanism pivotally mounted at one end on said proximal end of said power/video module to pivot relative thereto, and said display is pivotally mounted on an opposed end of said pivot arm to pivot relative thereto so as to be manually positioned in selective angular positions to allow external visualization of the patient's upper airway by the operator from various distances from and positions around the patient during insertion and intubation procedures.

7. The two-piece digital video laryngoscope according to claim 6, wherein said display image decoding circuitry is connected with said rechargeable battery power source and electrical and video circuitry by an electrical and image data conduit extending through said tubular pivot arm mechanism.

8. The two-piece digital video laryngoscope according to claim 6, wherein said tubular pivot arm mechanism comprises a central tubular member with a first transverse pivot rod at said one end pivotally mounted on the proximal end of said housing to pivot laterally with respect to said housing, and a second transverse pivot rod at said opposed end disposed in a plane normal to said first pivot rod pivotally mounted on said display frame to allow said display to be selectively positioned at angular positions relative to a vertical plane.

9. The two-piece digital video laryngoscope according to claim 1, wherein said digital image sensor is selected from the group consisting of a CMOS digital image sensor (complementary metal oxide semiconductor), and a CCD (charge-coupled device).

10. The two-piece digital video laryngoscope according to claim 1, wherein said flat panel display is selected from the group consisting of a LCD (liquid crystal display), and a PDP (plasma display panel).

* * * * *